(12) United States Patent
McNeill et al.

(10) Patent No.: US 8,801,254 B2
(45) Date of Patent: Aug. 12, 2014

(54) MEDICAL APPARATUS

(75) Inventors: Andrew McNeill, Cellardyke (GB); Paul Hayton, Bristol (GB); Chris Althorpe, Cardiff (GB)

(73) Assignee: Ambicare Limited, Cellardyke (GB)

( * ) Notice: Subject to any disclaimer, the term of this patent is extended or adjusted under 35 U.S.C. 154(b) by 230 days.

(21) Appl. No.: 13/381,962

(22) PCT Filed: Apr. 29, 2010

(86) PCT No.: PCT/GB2010/050703
§ 371 (c)(1),
(2), (4) Date: Mar. 8, 2012

(87) PCT Pub. No.: WO2011/004170
PCT Pub. Date: Jan. 13, 2011

(65) Prior Publication Data
US 2012/0155057 A1   Jun. 21, 2012

(30) Foreign Application Priority Data
Jul. 7, 2009   (GB) .................................. 0911740.9

(51) Int. Cl.
*F21V 5/00* (2006.01)
*A61N 5/06* (2006.01)

(52) U.S. Cl.
CPC ........................................ *A61N 5/06* (2013.01)
USPC ................ 362/572; 362/249.04; 362/249.09; 362/249.1; 607/87; 607/88

(58) Field of Classification Search
USPC .................... 362/572, 249.04, 249.09, 249.1; 607/87, 88
See application file for complete search history.

(56) References Cited

U.S. PATENT DOCUMENTS

| | | | |
|---|---|---|---|
| 5,616,140 A | 4/1997 | Prescott | |
| 6,290,713 B1 * | 9/2001 | Russell | 607/88 |
| 6,743,249 B1 * | 6/2004 | Alden | 607/88 |
| 7,052,167 B2 * | 5/2006 | Vanderschuit | 362/572 |
| 7,686,839 B2 * | 3/2010 | Parker | 607/93 |
| 2002/0143373 A1 * | 10/2002 | Courtnage et al. | 607/91 |
| 2003/0009205 A1 | 1/2003 | Biel | |
| 2004/0127961 A1 * | 7/2004 | Whitehurst | 607/88 |
| 2006/0173514 A1 * | 8/2006 | Biel et al. | 607/88 |
| 2006/0217787 A1 * | 9/2006 | Olson et al. | 607/88 |
| 2007/0239232 A1 | 10/2007 | Kurtz et al. | |
| 2008/0058689 A1 * | 3/2008 | Holloway et al. | 602/42 |
| 2009/0198173 A1 * | 8/2009 | Samuel et al. | 604/20 |
| 2010/0217358 A1 * | 8/2010 | Hebert et al. | 607/88 |

FOREIGN PATENT DOCUMENTS

WO   WO 2007/106856   9/2007

OTHER PUBLICATIONS

International Search Report for PCT/GB2010/050703 mailed on Jul. 7, 2010.

* cited by examiner

*Primary Examiner* — Ali Alavi
(74) *Attorney, Agent, or Firm* — Womble Carlyle Sandridge & Rice, LLP; Mark D. Jenkins (57) ABSTRACT

There is herein described medical apparatus. More particularly, there is herein described medical apparatus capable of adapting and/or conforming to a non-planar surface on a patient's body.

20 Claims, 6 Drawing Sheets

Fig. 6

MEDICAL APPARATUS

CROSS REFERENCE TO RELATED APPLICATIONS

This application claims priority to PCT Application Number PCT/GB2010/050703, with an international filing date of Apr. 29, 2010, which claims priority to United Kingdom Patent Application No. 0911740.9, filed Jul. 7, 2009, each of which is herein incorporated by reference in its entirety.

FIELD OF THE INVENTION

The present invention relates to medical apparatus. More particularly, the present invention relates to medical apparatus capable of adapting and/or conforming to a non-planar surface on a patient's body.

BACKGROUND OF THE INVENTION

Traditional light sources are typically rigid structures and are not flexible. Moreover, these types of traditional light sources contain electronics which further adds to their rigidity. Therefore, in applications where a flat light source is required to conform to a neighbouring surface, this lack of flex limits the degree of conformability. Traditional light sources that do flex have been found to be prone to breaking (or disconnecting from electronics) when folded past a certain angle.

Light can be used to treat a wide variety of diseases. When light alone is used to treat a disease, the treatment is referred to as phototherapy. Light may be used in conjunction with a pharmaceutical in which case the treatment is called photodynamic therapy.

Phototherapy and photodynamic therapy can be used to treat a variety of skin and internal diseases. In photodynamic therapy, a light-sensitive therapeutic agent known as a photopharmaceutical is supplied externally or internally to an area of the body which is to be treated. That area is then exposed to light of a suitable frequency and intensity to activate the photopharmaceutical. A variety of photopharmaceutical agents are currently available. For example there are topical agents such as 5-aminolevulinic acid hydrochloride (Crawford Pharmaceuticals), methylaminolevulinic acid (Metfix (Trade Mark), Photocure). Often, the drug is applied in a non-active form that is metabolised to a light-sensitive photopharmaceutical.

In photodynamic therapy, the primary technique for supplying light to the photopharmaceutical is to project light of a suitable wavelength from standalone light sources such as lasers or filtered arc lamps. These sources are cumbersome and expensive, and are therefore only suitable for use in hospitals. This leads to inconvenience for the patient, and high cost for the treatment. High light irradiances are needed in order to treat an acceptable number of patients per day (for the treatment to be cost effective) and to avoid unduly inconveniencing the patient.

It is an object of at least one aspect of the present invention to obviate or mitigate at least one or more of the aforementioned problems.

It is a further object of at least one aspect of the present invention to provide apparatus capable of providing therapeutic and/or cosmetic treatment and wherein the apparatus is capable of adapting and/or conforming to a non-planar surface on a patient's body.

It is a yet further object of at least one aspect of the present invention to provide medical apparatus comprising a light source and electronics wherein said medical apparatus is capable of adapting and/or conforming to a non-planar surface on a patient's body.

SUMMARY OF THE INVENTION

According to a first aspect of the present invention there is provided an apparatus for use in therapeutic and/or cosmetic treatment, the apparatus comprising:
a casing;
electronics located within or attached to the casing;
at least one light source;
a chassis located within the casing wherein along at least part of or substantially the whole length of the chassis there are channels on at least one or both sides of the chassis which are capable of supporting a flexible electronic substrate; and
wherein the casing and electronic substrate are capable of adapting and/or conforming to a non-planar surface.

The present invention may therefore utilise the channels (e.g. runners) on at least one or both sides of the chassis to allow a flexible substrate to be free or substantially free to move along the channels (e.g. runners).

Typically, the electronics, at least one light source and the flexible electronic substrate may be of the same device i.e. a unitary single component which forms the electronics, at least one light source and the flexible electronic substrate.

The channels may be set within the chassis which may comprise an upper and lower part. The flexible electronic substrate may be located and sit within the channels on either side of the chassis.

The chassis may comprise an upper and lower portion with the electronics, at least one light source and the flexible electronic substrate located within either of the upper and lower portions.

The function of the channels may be to allow the flexible electronic substrate to be free or substantially free to move along the channels (e.g. runners). This may allow the upper chassis and lower chassis to bend in tandem or substantially in tandem with the flexible electronic substrate being free or substantially free to move. This has the advantage in maintaining the distance in the apparatus between the flexible electronic substrate, diffusers and/or light sources and thereby providing increased light homogeneity for the emitted light whilst the device is flexed to conform to the treatment area. The channels therefore allow a stable light system to be set up in the apparatus with substantially constant distances being maintained between the flexible electronic substrate, diffusers and/or light sources.

The flexible electronic substrate may be any suitable substrate such as a printed circuit board (PCB).

The apparatus may also comprise at least one or more diffusers. Typically, there may be two or at least two or more diffusers.

By allowing the chassis to bend in tandem or substantially in tandem with the flexible electronic substrate allows the distance between the flexible electronic substrate and the at least one or more diffusers to be kept constant or substantially constant. This has the technical advantage of providing improved light homogeneity as the distance may be maintained between the flexible electronic substrate and the one or more diffusers. This therefore allows a constant light system to be maintained as the apparatus is bent and/or flexed.

The diffusers may also be arranged and/or located so that these may also be free or substantially free to move along the channels in the lower chassis.

In an alternative embodiment there may be a first protruding member (e.g. a post) located in a chassis of the apparatus which may function as a runner for a flexible substrate (e.g. a PCB or OLED). There may also be a second protruding member which typically does not function as a runner. The flexible electronic substrate may comprise a cut-away area (e.g. a notch) through which the first protruding member may extend. The cut-away area may allow the flexible electronic substrate to move relative to the post when the apparatus is flexed. The post may therefore sit within the cut-away area in the flexible electronic substrate. As the chassis is flexed, the flexible substrate may flexe with it, thereby ensuring that the distance between the electronic substrate and the diffuser is kept substantially constant. The flexible electronic substrate may therefore be able to move along the runner post allowing the chassis and the flexible electronic substrate to flex in tandem or substantially in tandem. The casing may also comprise at least one or a series of hinges which may allow the apparatus to bend and/or flex.

The casing may restrict the amount of conformation of the electronics.

Typically, the casing may surround at least part or preferably all of the electronics and/or the light source.

The apparatus of the present invention may therefore provide a light source which is capable of adapting and/or conforming to a non-planar, substantially non-planar or curved surface on, for example, any part of a human or mammal body such as on a foot, leg, torso, shoulder, arm, hand, head or facial area of a patient.

By allowing the casing to adapt and/or conform to a non-planar or curved surface allows the light source to be capable of providing even or substantially even illumination of a patient's skin, which is important for efficacious therapy.

The present invention may therefore allow a semi-rigid light source to adapt and/or conform to non-planar and/or curved surfaces on a patient. By having one or more light diffusers increases the homogeneity of the light being emitted from the apparatus.

The casing may have means of restricting the amount of conformability that it is capable of achieving. This would prevent the electronics from being flexed to such a degree that they break or fail.

The present invention may utilises at least one or more light diffusers which in combination are capable of providing improved homogeneity for illumination provided by the at least one light source.

There may be a plurality of light sources located within the casing. For example, the light sources may any suitable form of diode (e.g. LEDs).

The apparatus may comprise a double diffuser wherein both diffusers may be oriented in a parallel or substantially parallel orientation. There may be three or more or a plurality of light diffusers which may be in a parallel or substantially parallel orientation.

The diffusers may be located in a chassis using any form of suitable attachment means such as mechanical and/or adhesive means. The chassis may be flexible thereby allowing the apparatus to adapt and/or conform to a non-planar surface such as on a patient.

The diffusers in the apparatus may be separated by about 1-10 mm (e.g. about 4 mm) and may be any suitable type of diffusers that have the ability to improve the homogeneity of the light illumination from the light sources. The diffusers may have a thickness of about 0.1-1 mm (e.g. about 0.3 mm) and may be substantially transparent to light.

The casing may comprise an upper chassis and a lower chassis within which the light emitting apparatus may be located. Within the casing there may be a PCB which may be flexible. A member (e.g. a tubular member) may be used to house electronics for operating the apparatus.

The chassis such as the lower chassis may also comprise at least one or a series of hinges which may allow the apparatus to bend. The hinges may be of any suitable form but are capable of allowing the apparatus to adapt and/or conform to a non-planar surface. The chassis itself may also be flexible.

The casing may comprise a surface intended to make contact with a patient (i.e. a contact surface). This contact surface may be capable of bending, flexing and/or conforming around a non-planar, substantially non-planar or curved surface of, for example, a patient.

The casing may be capable of bending, flexing and/or conforming away from a planar position by less than about 5 degrees, less than about 10 degrees, less than about 15 degrees, less than about 20 degrees, less than about 25 degrees, less than about 30 degrees, less than about 35 degrees, less than about 40 degrees, less than about 45 degrees, less than about 50 degrees, less than about 55 degrees, less than about 60 degrees, less than about 65 degrees, less than about 70 degrees, less than about 75 degrees, less than about 85 degrees or less than about 90 degrees. Alternatively, the casing may be capable of bending, flexing and/or conforming away from a planar position by about 0-5 degrees, about 0-10 degrees, about 0-15 degrees, about 0-20 degrees, about 0-25 degrees, about 0-30 degrees, about 0-35 degrees, about 0-40 degrees, about 0-45 degrees, about 0-50 degrees, about 0-55 degrees, about 0-65 degrees, about 0-70 degrees, about 0-75 degrees, about 0-80 degrees, about 0-85 degrees or about 0-90 degrees. As indicated above the casing may comprise a surface intended to make contact with a patient (i.e. a contact surface) and it may be this surface which may be capable of bending, flexing and/or conforming away from a planar position.

The casing may also comprise means that once the casing is flexed, bent and/or conformed from an initial configuration (e.g. planar), this means urges the casing back to the initial configuration, for example, by a spring-type arrangement.

In a particular embodiment, the casing may comprise two sections, for example, an upper section and a lower section. Alternatively, there may be a plurality of sections. The two sections of the casing may be attached to one another during use using any suitable mechanical and/or adhesive means. For example, the two sections of the casing may be attached to one another using attachment means such as a snap-fit arrangement, clips, hooks, Velcro (Trade Mark) and the like. In at least one or both of the two sections of the casing, there may be means allowing the casing to bend, flex and/or conform. Typically, there may be at least one or two flexible portions in at least one or both of the two sections of the casing. There may also be a plurality of flexible portions. Typically, the flexible portion may be a hinge. In particularly preferred embodiments, there may be at least two or a plurality of hinges on at least one or both of the sections of the casing.

Typically, the casing may also comprise means which may restrict the amount by which the casing or a surface intended to make contact with a patient is capable of bending, flexing and/or conforming away from a planar arrangement. The casing may therefore comprise a form of stop means capable of restricting the amount of movement allowed. By restricting the amount of bending, flexing and/or conforming reduces any possible damage to electronics and a light source located within the casing.

The casing may comprise electronics for the operation of the apparatus and the light source. The casing may also be designed to allow light from the light source to exit from the casing and be used in medical applications such as therapeutic and/or cosmetic treatment. The casing may therefore be capable of distributing light over an area of a patient to be treated.

The surface of the casing intended to make contact with a patient may have a surface area of about 1-500 $cm^2$, about 1-250 $cm^2$, about 1-100 $cm^2$, about 1-100 $cm^2$ or about 5-50 $cm^2$. Alternatively, the surface of the casing intended to make contact with a patient may have a surface area of greater than about 1 $cm^2$, greater than about 5 $cm^2$, greater than about 10 $cm^2$, greater than about 50 $cm^2$ or greater than about 100 $cm^2$.

Conveniently, the casing may be made from any suitable material (e.g. biocompatible) such as any suitable plastics material, composite and/or metal based material. The material forming the casing may be pliable and may bend, flex and/or conform.

The casing may also comprise an adhesive sheet around at least part or the entire periphery of the casing. The adhesive sheet may provide an adhesive surface for attaching the apparatus to a patient. The combination of a casing capable of adapting to a non-planar and/or curved surface with a flexible adhesive periphery increases the number of sites that the apparatus may be attached to.

The apparatus may also comprise a transparent drug and/or chemical source capable of delivering drugs and/or chemicals to the area of the patient to be treated. The apparatus of the present invention may therefore be capable of performing a therapeutic and/or cosmetic treatment.

The present invention may therefore relate to a light emitting apparatus capable of performing a therapeutic and/or cosmetic treatment on a human or animal patient using photodynamic therapy or phototherapy. In some situations the treatment may be said to be of therapeutic nature (e.g. skin cancer, serious acne) whereas in other situations the treatment may be said to be of cosmetic nature (e.g. minor amounts of acne, anti-aging treatments such as treatment of wrinkling).

The light source may be any suitable light source that may emit light over a desired wavelength but may preferably be an array of LEDs on an array. The light source may be provided as a light emitting layer.

Typically, the light source may operate within a range of about 200-3000 nm, about 200-1500 nm, about 200-800 nm or about 250-750 nm. In particular embodiments the light source may operate in the visible region of the electromagnetic spectrum. Alternatively, the light source may operate in the ultraviolet or infrared wavelength regions of the electromagnetic spectrum. The light source during operation may operate at a substantially constant and/or uniform wavelength or alternatively may be scanned over a range of wavelengths. In particular embodiments more than one wavelength of light may be emitted and/or pulsed at the same or different times. This may be suitable for the treatment of acne.

The light source may have an extensive light emitting surface area of about 1-500 $cm^2$, about 1-250 $cm^2$, about 1-100 $cm^2$, about 1-100 $cm^2$ or about 5-50 $cm^2$. Alternatively, the light source may have a light emitting surface of greater than about 1 $cm^2$, greater than about 5 $cm^2$, greater than about 10 $cm^2$, greater than about 50 $cm^2$ or greater than about 100 $cm^2$.

The light source may be substantially square or substantially rectangular and may have dimensions of about 1 cm×1 cm, about 2 cm×2 cm, about 5 cm×5 cm, about 10 cm×10 cm or about 20 cm×10 cm. Alternatively, the light source may be substantially circular and may have a diameter of about 0.5 cm, about 1 cm, about 2 cm, about 5 cm, about 10 cm or about 20 cm.

The light source may emit light substantially continuously over a pre-set period of time or may emit light discontinuously such as in a pulsed manner. In particular embodiments, the light from the light source may be pulsed with a period of at least about 10 ms, at least about 100 ms, at least about 1 s, at least about 10 s, at least about 10 ms, at least about 100 s, at least about 1,000 s or at least about 10,000 s.

In particular embodiments, the light source may, for example, be any suitable form of diode such as organic light-emitting diode or an inorganic light-emitting diode incorporated into, for example, a diffuser. Alternatively, the light source may be a fluorescent light source such as a fluorescent lamp. The fluorescent light source may be compact in shape. For example, this includes technology developed from back-lit display technology, LEDs and waveguides and diffusers.

The light source may have an optical power density of about 0.1-500 $mW/cm^2$, about 1-200 $mW/cm^2$ or about 5-75 $mW/cm^2$. The light source during operation may operate at a substantially constant power or alternatively may be varied over a range of powers.

The apparatus may comprise a photochemical and/or a photopharmaceutical preparation in the drug and/or chemical source in the form of, for example a layer.

The photochemical and/or photopharmaceutical preparation may be delivered to the area of the patient to be treated at appropriate pre-set times and/or may be controlled by a control unit. The photochemical and/or a photopharmaceutical preparation may be present in the form of, for example, a gel, ointment, cream or gauze soaked in a photodynamic therapy solution. Alternatively, or in addition the light emitting device may be provided with a thin film impregnated with a photochemical and/or photopharmaceutical preparation. The photochemical and/or a photopharmaceutical preparation may comprise a drug and/or antiseptic capable of treating a patient which may be applied to a person in need thereof. Typically, the photochemical and/or photopharmaceutical may be transparent or substantially transparent or may become transparent or substantially transparent during use and emission of light.

In embodiments where the photochemical and/or photopharmaceutical may be transparent or translucent to the wavelength of the irradiating light, the resulting device may be readily applied without a separate step of applying a photochemical and/or a photopharmaceutical to a patient. In particular embodiments, the photochemical and/or photopharmaceutical may be covered with a peelable release medium. The photochemical and/or photopharmaceutical preparation may comprise an inactive compound which may be metabolised in vivo to an active compound. During use a suitable amount of the photochemical and/or photopharmaceutical preparation may be applied to an area of a patient to be treated.

Typical drugs and/or chemicals used in the present invention include but are not limited to precursor drugs such as ALA or Metfix or other photodynamic therapy agents.

In use, the drug and/or chemical layer may be placed over the top of the area of the patient to be treated. The chemical layer may be a moisturiser. To facilitate treatment an electrolyte solution such as sodium chloride solution may be placed on the skin to improve the electrical contact.

A power source may be supplied to power the light source and/or the electronics within the casing. The power source may be small and compact and may be integrated into the whole apparatus therefore making the apparatus suitable for ambulatory treatment. The apparatus of the present invention may therefore be wearable and may be attached to a foot, leg, torso, shoulder, arm, hand, head or facial area of a patient.

The apparatus may comprise attachment means for attaching the device to a body part(s) of a human or animal. For example, the apparatus may comprise mechanical and/or adhesive means for attaching the device to a body part of a human or animal. In particular embodiments, the apparatus may therefore comprise a strap arrangement which may optionally comprise a fastening means and/or Velcro (Trade Mark) and/or an adhesive surface for attaching the apparatus to the patient.

The apparatus may be lightweight and portable. In particular embodiments the apparatus may be a totally self-contained portable unit and may comprise a self-contained power supply. The power supply may operate electronics in the device and the light source. The apparatus may be sufficiently portable to enable ambulatory treatment therefore allowing treatment during which a patient may move around. Treatment may therefore occur at home or at work and may be removed by a patient when necessary. This provides lower treatment costs as this avoids out-patient or in-patient stays in hospital. This provides the significant advantage that lower light levels may be used since exposure can occur for a longer period of time. This overcomes the problem of pain induced in some patients by high irradiances from conventional sources used in hospitals. Moreover, lower irradiance over a longer period of time may be more effective in photoinduced therapy as it gives more time for oxygen to diffuse to the region to be treated, and reduces photobleaching of the photopharmaceutical.

The light source may also comprise a substrate layer such as a transparent or at least a substantially transparent substrate layer. Alternatively, the light source may comprise a translucent or at least a substantially translucent substrate layer. The substrate layer may function as a support layer for the light source and may allow the light to penetrate there through. The substrate layer may also function as a barrier layer too and may be selected to prevent oxygen and/or moisture from penetrating the light source. The substrate layer may be made from or comprise any one of or combination of suitable materials such as a glass, plastics or polymer. Additional layers may also be present.

The apparatus according to the present invention may be used in a range of phototherapies and photodynamic therapies. For example, the apparatus according to the present invention may be used in the treatment of cancer (e.g. skin cancer), acne, wrinkles, wound-healing, anti-aging and post-skin laser treatments such as found in cosmetic applications. By wound is meant any form of open or closed wound. Open wounds include but are not limited to: incisions or incised wounds; lacerations; abrasions; puncture wounds; penetration wounds; gunshot wounds; and ulcers (including diabetic derived ulcers). Closed wounds include but are not limited to: contusions; hemaomas; and crushing injuries.

According to a second aspect of the present invention there is provided a method of performing a therapeutic and/or cosmetic treatment, the method comprising:
  providing a casing;
  providing electronics located within or attached to the casing;
  providing at least one light source;
  a chassis located within the casing wherein along at least part of or substantially the whole length of the chassis there are channels on at least one or both sides of the chassis which are capable of supporting a flexible electronic substrate; and
    wherein the casing and electronic substrate are capable of adapting and/or conforming to a non-planar surface.

The method may be performed by an apparatus as defined in the first aspect.

According to a third aspect of the present invention there is provided use of an apparatus according to the first aspect in a medical treatment.

Typically, the medical treatment may be a photodynamic therapy or phototherapy.

The present invention may therefore relate to the treatment of cancer (e.g. skin cancer), acne, wrinkles, wound-healing, anti-aging and post-skin laser treatments (e.g. cosmetic applications).

According to a fourth aspect of the present invention there is provided a method of medical treatment using of an apparatus according to the first aspect.

The medical treatment may be that of photodynamic therapy or phototherapy.

Moreover, the treatment may be that of the treatment of cancer (e.g. skin cancer), acne, wrinkles, wound-healing, anti-aging and post-skin laser treatments (e.g. cosmetic applications).

BRIEF DESCRIPTION OF THE DRAWINGS

Embodiments of the present invention will now be described, by way of example only, with reference to the accompanying drawings in which.

BRIEF DESCRIPTION

The present invention relates to an apparatus capable of performing a therapeutic and/or cosmetic treatment on a human or animal patient. The apparatus may be used for any type of medical treatment and, for example, may be used in phototherapy or photodynamic therapy.

Figure 1:
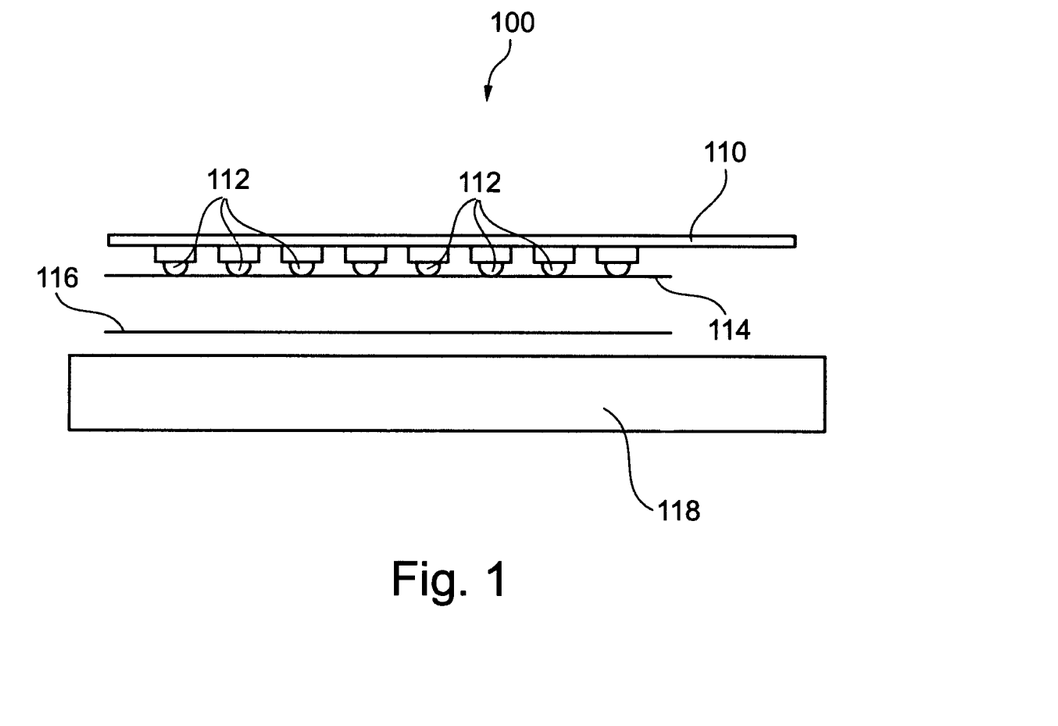
FIG. 1 is a schematic representation of an apparatus according to an embodiment of the present invention showing the position of two diffusers.

FIG. 1 is a representation of an apparatus according to the present invention, generally designated 100. As shown in FIG. 1 the apparatus 100 comprises a PCB 110 attached to which there are a plurality of light sources 112 (e.g. LEDs or OLEDs) and two light diffusers 114,116. The apparatus is shown placed on a skin surface 118. The apparatus 100 has a double diffuser wherein there are two diffusers 114,116 which are oriented in a substantially parallel orientation to a skin surface. Although not shown there may be more than two diffusers which may be positioned in a substantially parallel orientation. The diffusers 114,116 may be located in a chassis (not shown) using any form of suitable attachment means. The chassis may be flexible thereby allowing the apparatus 10 to adapt and/or conform to a non-planar surface such as on a patient.

The diffusers 114,116 in the apparatus 100 may be separated by about 1-10 mm (e.g. about 4 mm) and may be any suitable type of diffusers that have the ability to improve the homogeneity of the light illumination from the plurality of light sources 112. The diffusers have a thickness of about 0.3 mm and are substantially transparent to light.

Figure 2:
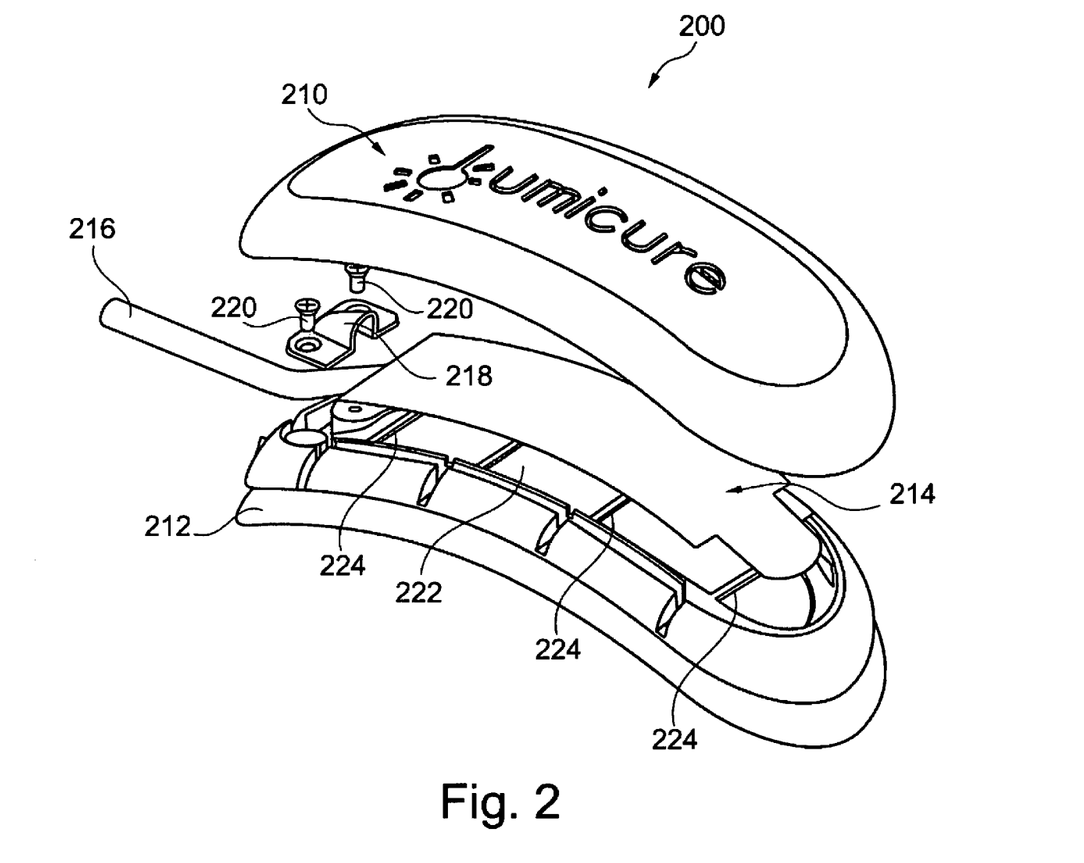
FIG. 2 is an exploded view of apparatus according to a further embodiment of the present invention.

FIG. 2 is a representation of an apparatus 200 which may be used in phototherapy or photodynamic therapy. The apparatus 200 comprises a casing that is made up of an upper chassis 210 and a lower chassis 212 within which the light emitting apparatus is located. As shown in FIG. 2 there is a flexible PCB 214 which is attached to a tubular member 216 within which wires may be used to connect to electronics for operating the apparatus 200. There is also shown an attachment element 218 which is connectable to the lower chassis 212 using two screws 220. The attachment element 218 prevents the tubular member 216 from being pulled out. FIG. 2 also shows that the lower chassis 212 comprises a flexible diffusing layer 222 within which the flexible PCB 214 may be located. The lower chassis also comprises a series of hinges 224 which allow the apparatus 200 to bend.

Figure 3:
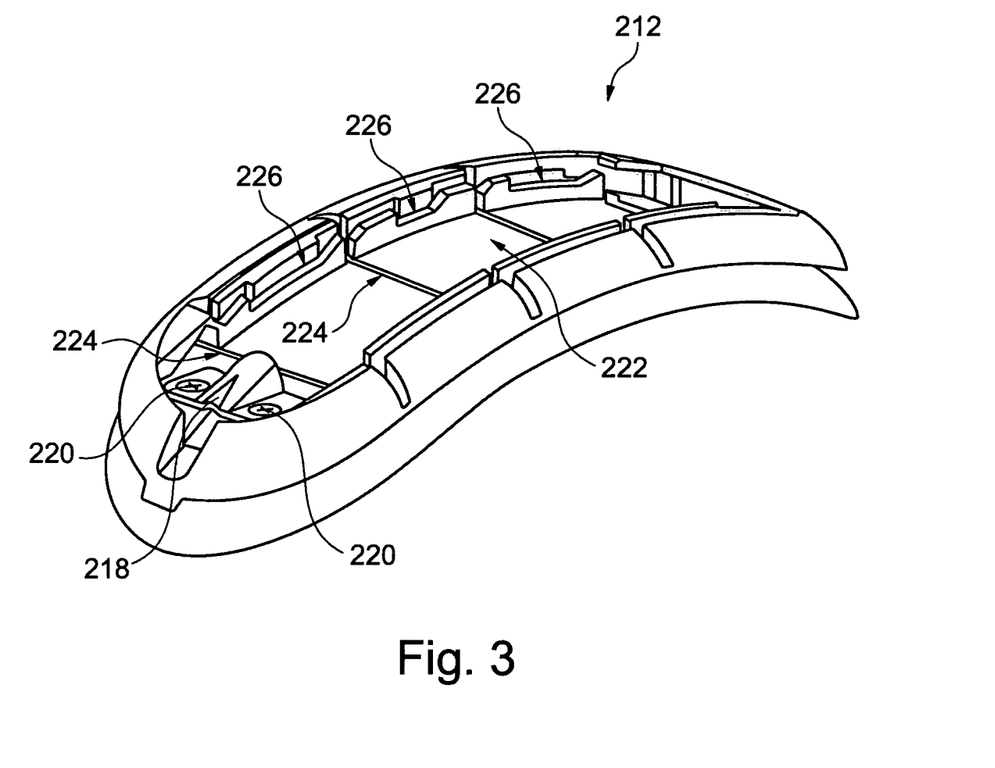
FIG. 3 is a view of a lower part of the apparatus shown in FIG. 2.

FIG. 3 is a view of the lower chassis 212 of the apparatus 200. The attachment element 218 is shown attached using the two screws 220. The tubular member 216 is omitted for clarity purposes. FIG. 3 shows the flexible diffusing layer 222 within which the flexible PCB 214 may be located. The series of hinges 224 are also shown which allow the apparatus 200 to bend.

FIG. 3 also shows that running along the length of the lower chassis 212 there are channels 226 (e.g. runners) on either side. The channels 226 are set within the chassis 212 and within the channels on either side of the lower chassis 212 sits the flexible PCB 214. FIG. 3 also clearly shows the series of hinges 224 that allow the apparatus to bend and/or adapt and/or conform to a non-planar surface such as on a patient. As the apparatus bends and/or adapts and/or conforms to a non-planar surface the PCB is free or substantially free to move along the channels 226 (e.g. runners). This allows the upper chassis 210 and lower chassis 212 to bend in tandem or substantially in tandem. This allows the distance to be maintained to the diffusers which improves homogeneity during bending and/or flexing of the device. Although not shown in FIG. 3, there are two diffusers located within the lower chassis 212. In the present invention when the apparatus is flexed the PCB 214 is therefore free to move along the channels 226. The diffusers may also be arranged so that these may also be free to move along the channels 226. This helps to maintain the orientation of the diffusers in a substantially parallel orientation with each other and also a skin surface to be treated.

Figure 4:
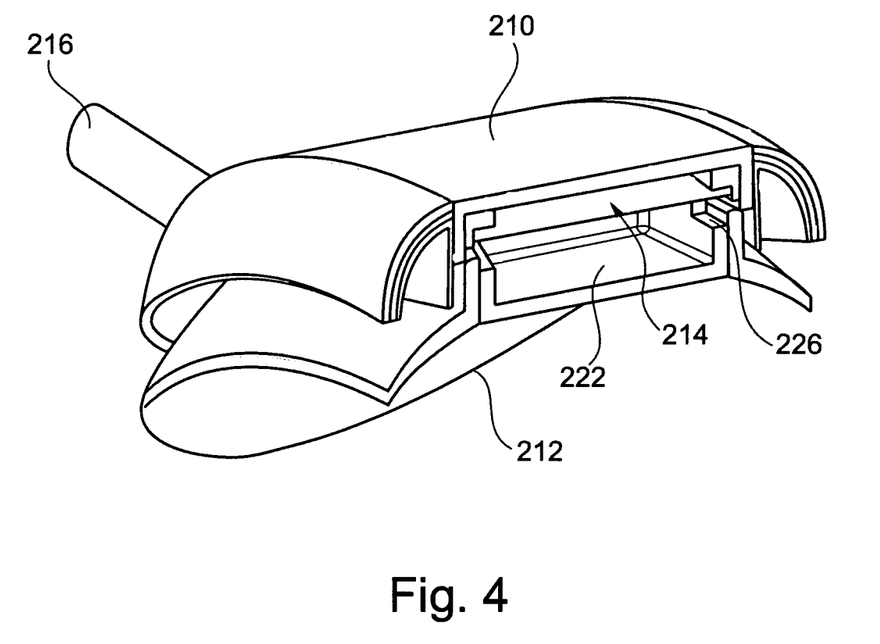
FIG. 4 is a sectional view of the apparatus shown in FIG. 2.

FIG. 4 shows the PCB 214 located on the channels 226 which act as runners and allows the PCB 214 to move when the apparatus 200 is flexed. In this embodiment, the PCB 214 may be seen as a male part and the channels 226 as a female part.

Figure 5:
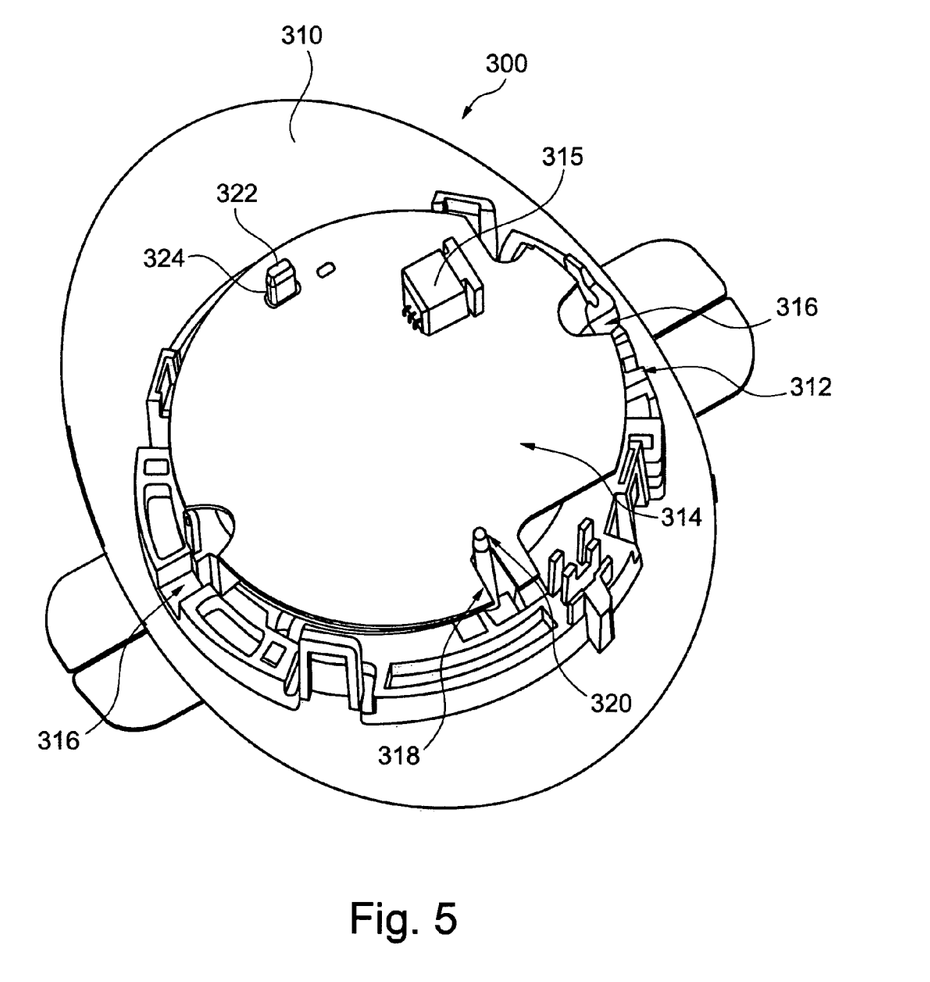
FIG. 5 is a view of apparatus according to a yet further embodiment of the present invention.

FIG. 5 is a representation of a further apparatus 300 which shows the apparatus 300 comprising a flexible base 310 (e.g. a plaster which may be adhesive). The apparatus 300 also comprises a chassis 312 and a flexible PCB 314. There is also shown a hinge 316 in the chassis 312. There is also a protruding member in the form of a post 320 in the chassis 312 which functions as a runner (e.g. a male runner). The post 320 extends through a notch 318 (e.g. a cut-away part) in the PCB 314 which allows the PCB 314 to move relative to the post 320 when the apparatus 300 is flexed. The post 320 therefore sits with the notch 318 of the PCB 314. The PCB is therefore not firmly held in the chassis 312 and is allowed to move with the post 320 controlling the movement of the PCB 314 by moving within the perimeter formed by the notch 318. The notch 318 is an open-ended hole. FIG. 5 also shows that there is a second post 322 which extends through an opening 324 in the PCB. However, the opening 324 does not comprise an open-ended notch allowing the post to move within it. The PCB 314 is therefore able to move along the runner post 320 allowing the chassis 312 and the PCB 314 to flex in tandem or substantially in tandem.

Figure 6:
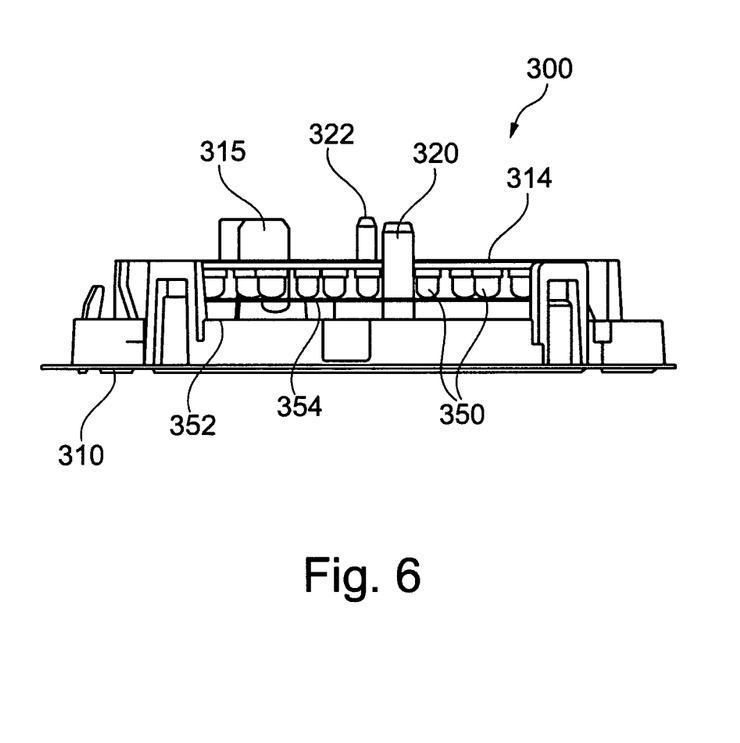
FIG. 6 is a sectional view of part of the apparatus shown in FIG. 5.

FIG. 6 shows the position of a series of light sources 350 (e.g. LEDs) within the apparatus 300. The light sources 350 are located above two diffusers 352, 354 which are separated by a small distance of about 1-10 mm (e.g. about 4 mm). There is also shown part of the electronic components 315. In this embodiment, the PCB 314 may be described as a female part and the runner (e.g. the post 32) located within the PCB 314 as a male part.

Whilst specific embodiments of the present invention have been described above, it will be appreciated that departures from the described embodiments may still fall within the scope of the present invention. For example, any suitable type of mechanism may be used to allow the casing to bend, flex and/or conform to a part of a patient's body. Moreover, any suitable type of light source may be used. Furthermore any suitable type of drug and/or antiseptic may be delivered using apparatus according to the present invention.

The invention claimed is:

1. Apparatus for use in therapeutic and cosmetic treatment, the apparatus comprising:
   a casing;
   electronics located within or attached to the casing;
   at least one light source;
   a chassis located within the casing wherein along at least part of or substantially the whole length of the chassis there are channels on at least one or both sides of the chassis which support a flexible electronic substrate; and
   wherein the casing and electronic substrate adapt and conform to a non-planar surface.

2. Apparatus according to claim 1, wherein the channels support the flexible electronic substrate and allowing the flexible electronic substrate to be free or substantially free to move along the channels.

3. Apparatus according to claim 1 wherein the channels allow an upper chassis and lower chassis to bend in tandem or substantially in tandem with the flexible electronic substrate being free or substantially free to move along the channels during bending and flexing.

4. Apparatus according to claim 1, wherein diffusers are also arranged and located in the casing so that the diffusers are free or substantially free to move along the channels.

5. Apparatus according to claim 1, wherein there is a protruding member in a chassis of the casing which functions as a runner for a flexible electronic substrate.

6. Apparatus according to claim 1, wherein the apparatus comprises a flexible electronic substrate which has a cut-away area (e.g. a notch) through which a protruding member is extendable and allows the flexible electronic substrate to move relative to the protruding member when the apparatus is bent and flexed.

7. Apparatus according to claim 5, wherein a flexible electronic substrate moves along the protruding member thereby allowing the chassis and the flexible electronic substrate to bend and flex in tandem or substantially in tandem.

8. Apparatus according to claim 1, wherein the casing comprises at least one or a series of hinges that allow the apparatus to bend and flex.

9. Apparatus according to claim 1, wherein there are at least two or more light diffusers which are capable of providing improved homogeneity for illumination provided by the at least one light source.

10. Apparatus according to claim 1, wherein there is a plurality of light diffusers.

11. Apparatus according to claim 1, wherein the two or more light diffusers are oriented in a parallel or substantially parallel orientation in the casing.

12. Apparatus according to claim 1, wherein there are three or more or a plurality of light diffusers which are in a parallel or substantially parallel orientation in the casing.

13. Apparatus according to claim 1, wherein there are two or more light diffusers located in a chassis using any form of suitable attachment means such as mechanical and adhesive means.

14. Apparatus according to claim 13, wherein the chassis is flexible thereby allowing the apparatus to adapt and conform to a non-planar surface such as on a patient.

15. Apparatus according to claim 1, wherein there is a plurality of light sources located within the casing.

16. Apparatus according to claim 1, wherein the light sources are LEDs or OLEDS, and wherein there are two or more light diffusers which are spaced apart by about 1-10 mm or about 4 mm.

17. Apparatus according to claim 1, wherein the casing comprises an upper chassis and a lower chassis within which the light emitting apparatus is located, and wherein located within the casing there is a flexible PCB.

18. Apparatus according to claim 1, wherein the casing comprises a series of hinges which are capable of allowing the apparatus to bend, and wherein the casing comprises a housing area within which a PCB is located.

19. Apparatus according to claim 1, wherein the apparatus comprises a drug and chemical source capable of delivering drugs and chemicals to an area of the patient to be treated, and wherein the channels maintain a constant or substantially constant distance between the at least one light source or a plurality of light sources and a light diffuser.

20. A method of performing a therapeutic and cosmetic treatment, the method comprising:
 providing a casing;
 providing electronics located within or attached to the casing;
 providing at least one light source;
 a chassis located within the casing wherein along at least part of or substantially the whole length of the chassis there are channels on at least one or both sides of the chassis which support a flexible electronic substrate; and
 wherein the casing and electronic substrate adapt and conform to a non-planar surface.

* * * * *